United States Patent [19]

Blurton et al.

[11] 4,073,698
[45] Feb. 14, 1978

[54] METHOD AND DEVICE FOR THE DETECTION AND MEASUREMENT OF CARBON MONOXIDE IN THE PRESENCE OF HYDROGEN

[75] Inventors: Keith F. Blurton, Yorktown; Joseph R. Stetter, Peekskill, both of N.Y.

[73] Assignee: Energetics Science, Inc., Elmsford, N.Y.

[21] Appl. No.: 692,919

[22] Filed: June 4, 1976

[51] Int. Cl.² .......................................... G01N 27/46
[52] U.S. Cl. ............................ 204/1 T; 204/195 R; 423/219; 423/248; 423/415 A
[58] Field of Search ........................ 204/1 K, 195 R; 423/219, 248, 415 A; 73/23; 23/232 E, 254 E

[56] References Cited

U.S. PATENT DOCUMENTS

| | | | |
|---|---|---|---|
| 2,826,480 | 3/1958 | Webster | 423/219 |
| 3,159,019 | 12/1964 | De Ford | 73/23 |
| 3,640,688 | 2/1972 | Walther | 23/232 E X |
| 3,776,832 | 12/1973 | Oswin et al. | 204/195 R |
| 3,880,722 | 4/1975 | Beltzer | 204/1 T |

*Primary Examiner*—G. L. Kaplan
*Attorney, Agent, or Firm*—Larson, Taylor and Hinds

[57] ABSTRACT

Carbon monoxide in gaseous samples containing hydrogen is detected by first heating the gas sample in an oxidizing atmosphere at a temperature of at least 700° C in a non-catalytic reaction zone to selectively oxidize the hydrogen to water and then passing the gaseous reaction products from the selective oxidation to a carbon monoxide analyzer.

9 Claims, 6 Drawing Figures

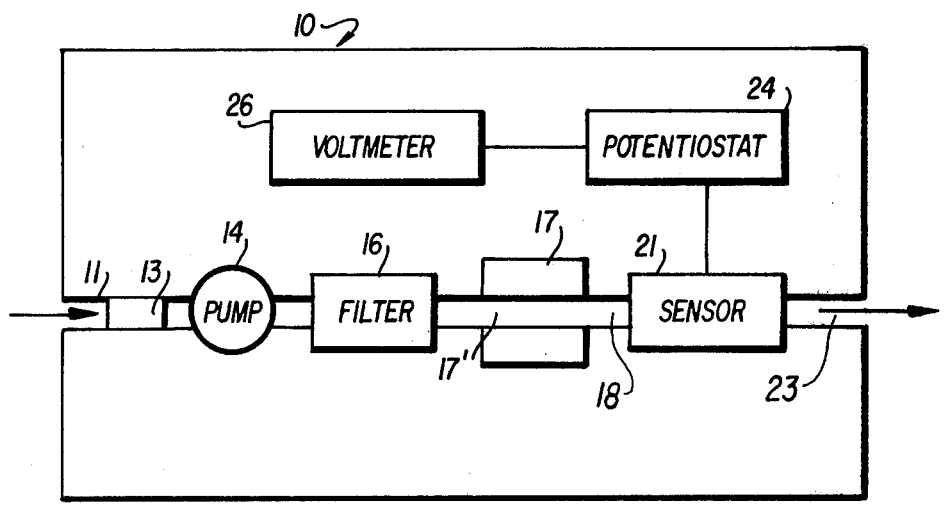
FIG. 1
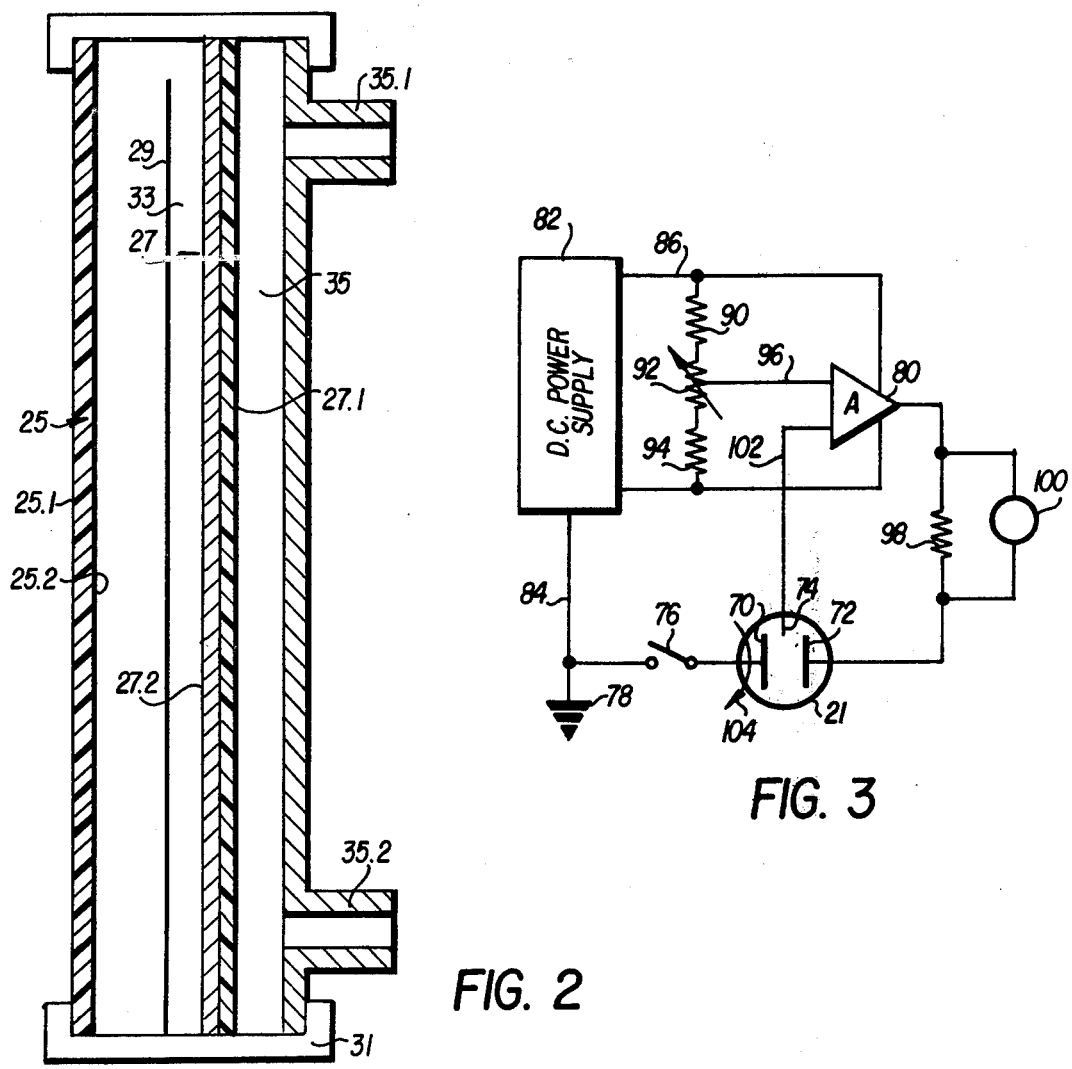
FIG. 2
FIG. 3

METHOD AND DEVICE FOR THE DETECTION AND MEASUREMENT OF CARBON MONOXIDE IN THE PRESENCE OF HYDROGEN

BACKGROUND OF THE INVENTION

1. Field of the Invention

The present invention relates to a method of separating hydrogen from gaseous mixtures containing hydrogen and carbon monoxide.

In another aspect, the invention is directed to the detection of carbon monoxide in the presence of interfering concentrations of hydrogen.

2. Discussion of the Prior Art

In order to meet the needs arising in connection with pollution control of carbon monoxide, extensive activity has been directed to the development and production of detection equipment useful in solving this problem. Exemplary of such equipment is that described by Oswin et al in U.S. Pat. Nos. 3,776,832 and 3,824,167. The sensitivity and effectiveness of this equipment described in the aforementioned patents, notwithstanding, it, as well as other prior art carbon monoxide detection systems, experiences difficulty in the accurate measurement of carbon monoxide when in the presence of high concentrations of hydrogen. A common example of this problem is found in the monitoring of carbon monoxide in submarines whose batteries are periodically charged resulting in the discharge or evolution of hydrogen into the atmosphere in concentrations as high as 3.0%. The presence of concentrations of hydrogen at these levels in the atmosphere to be tested creates a percent error in carbon monoxide measurement which is unacceptable.

In addition, the general criteria applied to measuring and testing equipment such as that of the present invention include requisites for portability, non-prohibitive cost, safety, and accuracy in measuring the quantity of the gas detected. In the prior art, it has been found difficult to simultaneously fulfill all of these requirements. Increasing the accuracy of measuring equipment has inherently involved an increase in either the size or the complexity of such equipment thereby disadvantageously affecting either the cost or portability or both. Quite often, problems related to simultaneous provision of these features have been decisive in obstructing the practical development and utilization of particular detection apparatus.

OBJECTS AND GENERAL DESCRIPTION OF THE INVENTION

Accordingly, a primary object of the present invention is to provide a compact, inexpensive and easy-to-operate device for accurately and reproducibly detecting and quantitatively determining the level of carbon monoxide in the presence of interfering concentrations of hydrogen.

It is another object of the invention to provide a method of separating hydrogen from gaseous mixtures containing carbon monoxide.

The aforesaid objects are obtained by heating a gas sample containing carbon monoxide and interfering concentrations of hydrogen in an oxidizing atmosphere at a temperature of at least 700° C, in a non-catalytic reaction zone. It has been unexpectedly found that subjecting the carbon monoxide and hydrogen-containing gas mixture to oxidation under the defined reaction conditions selectively oxidizes the hydrogen to water without substantial oxidation of the carbon monoxide.

The reaction conditions are critical, however, for if temperatures below about 700° C are employed the necessary selective oxidation of the hydrogen over the carbon monoxide is not obtained. It is essential, moreover, that a catalyst is not employed and that includes a reactor constructed of a material that would have a catalytic effect on the oxidative reaction. The use of a catalyst in the reaction even at temperatures of at least 700° C fails to provide selective oxidation of the hydrogen in the carbon monoxide/hydrogen-containing mixture. Thus, the reaction zone within the reactor or reactor chamber must be constructed of a non-catalytic material. By "non-catalytic material" as used herein and in the appended claims is meant an inert material which has substantially no catalytic effect on the oxidation reaction. Illustrative of suitable reactor materials are stainless steel, quartz and Vycor. The preferred reactors are the heat- and chemical-resistant glassware type materials such as Vycor. The reaction zone may be of any desired shape but as will be described below is preferably in the form of a tubular reactor.

Reaction temperatures up to the degradation temperature of the reactor material are contemplated by the invention. The preferred temperatures, however, generally will fall in the range of 700° C to 850° C. Elevated pressures can be used for the reaction if desired but ordinarily are unnecessary for the reaction proceeds smoothly and quickly under ambient or atmospheric pressure.

The water in the products resulting from the selective oxidation will be in the form of steam in admixture with the other gaseous components. Any convenient procedure known in the prior art can be employed to remove the water as, for instance, simply cooling the reaction product mixture to condense the water following the collection of the remaining off-gases.

In accordance with the aspect of the invention directed to the detection of carbon monoxide, the gaseous reaction products from the selective oxidation are introduced to a carbon monoxide analyzer. Illustrative of suitable carbon monoxide analyzers are electrochemical instruments of the type described, for instance, in U.S. Pat. Nos. 3,776,832 and 3,824,167. The devices described in these patents include a 3-electrode electrochemical system having an anode, a reference electrode, a cathode, and an aqueous electrolyte in contact with the anode, cathode and reference electrode, said anode having catalyst bonded to a hydrophobic material to provide a diffusion electrode. In these electrochemical instruments the gaseous reaction products from the selective oxidation are introduced to the anode of the cell which is maintained at a fixed potential of from about 0.7 to 1.5 volts with respect to the reversible hydrogen couple in the electrolyte of the cell. The current flowing between said anode and cathode of the cell is then measured to quantitatively determine the amount of carbon monoxide in said gaseous sample.

Accordingly, the apparatus of the present invention comprises a non-catalytic reaction zone having an inlet and an outlet, means for heating said reaction zone to a temperature of at least 700° C, in combination with a carbon monoxide analyzer, communications means between said analyzer and the outlet of said reaction zone, means for drawing said gas sample through said reaction zone and into said analyzer at a controlled flow rate and read out means for reading the quantity of carbon monoxide detected. The preferred carbon monoxide analyzer is a three-electrode electrochemical system having an electrochemical cell comprising an anode, a cathode, a reference electrode at which substantially no current flows and an aqueous electrolyte in contact with said anode, cathode and reference electrode, means for exposing said anode to said gas and means for maintaining said anode at a fixed potential relative to the reference electrode from about 0.7 to 1.5 volts with respect to the reversible hydrogen couple in the electrolyte in said cell.

The means in the preferred electrochemical cell for exposing the gaseous reaction products to the working or anode electrode is generally an anode chamber which preferably defines a labyrinthine path through which the gaseous reaction products are passed to the working electrode surface, as is described in the electrochemical cell of U.S. Pat. Nos. 3,776,832 and 3,824,167, hereby incorporated by reference. Other designs can be employed, however, it only being essential that the geometric working electrode surface area remain constant, or substantially constant and is fed with a predetermined quantity of gaseous reaction products over a predetermined period of time. In this regard, it is to be noted that insofar as the actual gas being detected is concerned, it is immaterial whether the flow rate is high or low.

The anode of the preferred electrochemical cell is comprised of catalyst capable of catalyzing electrooxidation of carbon monoxide, bonded to a suitable hydrophobic material, such as unsintered polytetrafluoroethylene (PTFE) to provide a lightweight diffusion electrode. The hydrophobic material may take the form of a binder for the catalyst, a sheet support therefor or both. For instance, the catalyst may be deposited as a layer directly to the surface of a hydrophobic sheet support or it may be admixed with a suitable hydrophobic binder and the admixture applied as a layer to a suitable support as, for instance, a suitable hydrophobic material such as PTFE, carbon or a metal. When an admixture of catalyst and hydrophobic binder is employed it can be supported with any suitable porous support substrate say of plastic, carbon, metal and the like. Suitable hydrophobic binder and/or support substrate materials include hydrophobic fluorocarbons such as polytetrafluoroethylene, polychlorotrifluoroethylene or the like, as well as less hydrophobic materials including polyacrylonitrile, polyvinylchloride, polyvinylalcohol, carboxymethyl cellulose, or the like. In general, it will be found that catalyst materials for the anode may be appropriately selected from the noble metals which include the platinum group metals such as platinum, palladium, rhodium, iridium, ruthenium, and osmium. The preferred catalytic material is platinum. As will be further apparent to one skilled in the art, when the support substrate is a hydrophobic material such as PTFE, the hydrophobic material must be oriented in the cell in order that the catalyst is in contact with the gas sample, with the catalytic layer being in contact with the electrolyte.

The specific structure of the cathode employed in the preferred electrochemical cell is not critical. It is only essential for the sensor that the cathode consist of a material at which electrochemical reduction occurs. The preferred cathode for the sensor is one which provides a site at which oxygen will be electrochemically reduced as, for example, platinum.

The reference electrode of the preferred electrochemical cell must be capable of maintaining a relatively constant potential in the environment of the electrochemical cell. Preferred reference electrodes are Pt-catalyzed air electrodes. The third or reference electrode can be positioned between the anode and cathode, or it can be positioned on the same plane or substrate as the cathode or anode. Preferably, however, in order to obtain greater compactness of the cell and due to optimum ion-transfer characteristics, and the like, the cathode and the third or reference electrode will be part of a common substrate. It is only necessary that the anode, cathode, and third electrode be electrically insulated from each other. Thus, a polymer substrate such as polytetrafluoroethylene can have two separate and distinct portions coated with a catalytic material such as platinum, or an admixture of platinum and PTFE particles. The entire substrate will, therefore, function as both the cathode and reference electrode. As will be more fully apparent hereinafter, various designs or layouts can be used.

Reference electrode, as the term is used herein, defines an electrode at which no, or substantially no, current flows. Accordingly, the reference electrode and working electrode, i.e., the anode must be connected through electronic circuitry, or the like, to preclude or minimize current flow between the reference electrode and working electrode, so as to define and maintain a known reference potential. Although it is virtually impossible to completely eliminate current flow, the reference potential cannot show extensive drift, i.e., more than about $\pm 25$ mV; or rapid drift, i.e., more than $\pm 5$ mV, over a period of 10 seconds. If extensive or rapid drift occurs, a false reading as to the quantity of the detected gas may be obtained. As is apparent, the actual extent of current drift depends upon the accuracy of the measurement needed. If high accuracy is unnecessary, a greater current drift can be tolerated.

The electrolyte in the preferred 3-electrode detection system of the invention can be either an aqueous acid or aqueous alkaline and can be either free-flowing or trapped in a suitable matrix. In the event a matrix is employed, the matrix material must be sufficiently hydrophilic to permit continuous wetting of the anode and cathode surfaces as well as the surface of the third or reference electrode. Materials such as asbestos, Kraft paper, polyvinylalcohol, polyvinylchloride which has been treated to render it hydrophilic, or the like, can be selected.

The means for drawing the gas sample through the reaction zone into the carbon monoxide analyzer will effectively pass a predetermined quantity of gaseous reaction products per unit time to a predetermined working electrode surface area, thus assuring continuous accuracy in the quantitative measurement. Preferably, the quantity of gas fed to the anode surface is controlled by a constant flow control means of the conventional type which feeds the gas sample to the carbon monoxide analyzer at a constant rate. The flow rate may vary with the only important criterion being that it provide the gas sample a residence time within the reactor sufficient to complete the selective oxidation reaction. Thus, the particular flow rate selected will be dependent primarily upon the length of the reaction zone. Flow rates of up to 400 cc/minute have been satisfactorily employed in portable systems and flow rates as high as 2 liter/minute are envisaged in such systems. A flow rate of 2 liters/minute is probably the maximum since otherwise the reactor will be of a size too large for use in portable units. The control of the flow rate can be accomplished in various ways including a flow meter positioned between the pump means and the inlet of the reaction zone.

Pumping or suction means are normally employed to draw both the gas sample and the resulting gaseous reaction products through the flow control means in metered amounts, optional filter means, reactor and carbon monoxide analyzer. The pump or suction means and flow control means can be of various commercial design and form no part of the present invention. The only criterion is that the pump or suction means have sufficient capacity to pull or push the gas sample through the flow control means, reaction zone and carbon monoxide analyzer and the flow control means must have precision sufficient to measure the volume being carried through the carbon monoxide analyzer (e.g., an electrochemical cell) with reasonable accuracy.

Means communicating the reaction zone outlet with the carbon monoxide analyzer can be any suitable connecting means of inert material, that is, a material which does not form soluble oxidizable products. Plastic tubing such as tubing of polyvinylchloride or copolymers thereof, for instance, has been found satisfactory.

Advantageously, other scrubbers or filters may be provided before the inlet of the reaction zone for the removal of other interfering gases such as sulfur oxides, hydrocarbons, nitrogen oxides and hydrogen sulfide that may be present in the gaseous medium which may give signals at the fixed potentials or interfere with the selective oxidation. Suitable filters for these materials include, for instance, Purafil ($KM_nO_4$ adsorbed on alumina).

The apparatus of the invention may be conveniently provided with a housing which can be made of any suitable material that does not form soluble, oxidizable products. Amongst these materials the preferred are plastics such as the olefinic polymers. The housing should be designed to permit the working electrode to have an area exposed to ambient air and can include all of the components of the system, including the reactor wherein the selective oxidation is performed. Alternatively, the reactor can be located outside the housing in the form of an attachment thereto.

BRIEF DESCRIPTION OF THE DRAWINGS

The method and detecting device of the present invention will be more readily apparent from the accompanying drawings wherein like numerals are employed to designate like parts. In the drawing:

FIG. 1 is a diagrammatic view in block form of a preferred device suitable for use in the detection and measurement of CO in the atmosphere;

FIG. 2 is a cross-sectional view of an electrochemical cell useful in the detector unit;

FIG. 3 is a schematic diagram of a potentiostat circuit for controlling operation of the cell and particularly as applied in maintaining a fixed potential between the working electrode and a reference electrode;

DETAILED DESCRIPTION OF PREFERRED EMBODIMENT

Figure 4:
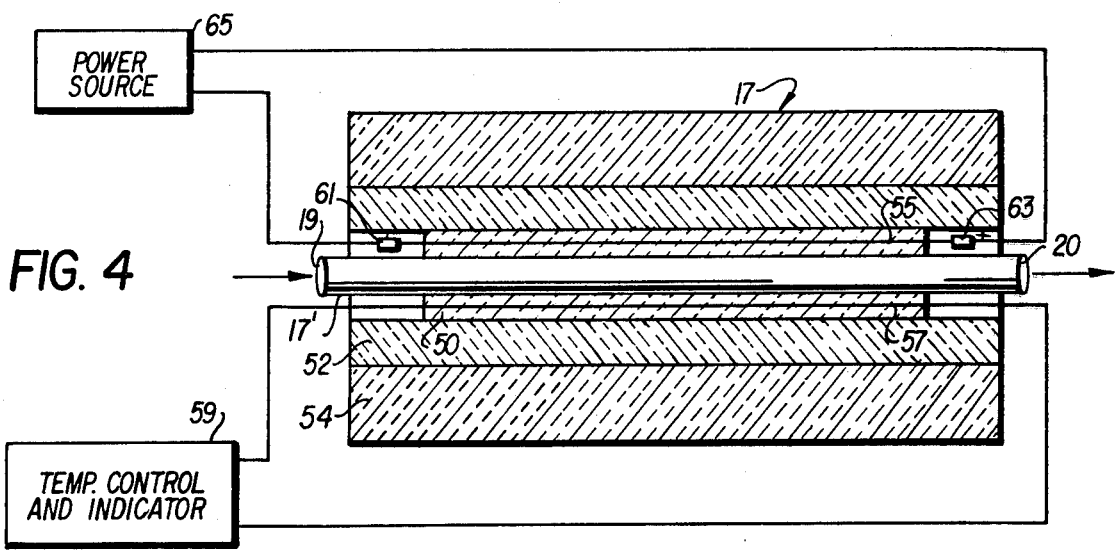
FIG. 4 is a cross-sectional view of a reactor useful in the selective oxidation step of the invention.

More specifically, referring to FIG. 1, the detecting device for the measurement of carbon monoxide is positioned without a housing 10. The device includes a sample intake means 11 in direct communication with a flow meter 13 which in turn is in communication with a pump 14. The pump 14 communicates with a filter 16 which in turn communicates with a reactor 17 containing a non-catalytic reaction zone shown in FIG. 4 and means, also shown in FIG. 4, for heating the reaction zone to a temperature of at least 700° C. Reactor 17 is connected via a plastic tube 18 of polyvinylchloride with an electrochemical cell designated sensor 21. The reaction gases from reactor 17 are pumped through sensor 21 and exit from the device via exhaust 23. The sensor 21 is provided with a potentiostat 24 for maintenance of the fixed relative potential between the anode and the reference electrode in sensor 21 and a voltmeter 26. The potentiostat is hooked up to an electronic circuit described below which includes an amplifier and voltmeter.

Sensor 21 as seen most clearly from FIG. 2, will include a cathode 25, an anode 27, and a third or reference electrode 29, all positioned within a housing 31. In the embodiment of FIG. 2, the cathode, anode, and third electrode are in contact with a free-flowing electrolyte 33. Adjacent anode 27 is reactant chamber 35 having reactant gas inlet 35.1 which is in direct communication with intake 11 and outlet 35.2. In the embodiment shown, cathode 25 is in direct communication with atmospheric air. Both the anode and cathode are lightweight electrodes comprising a hydrophobic plastic substrate 27.1 and 25.1 in direct contact with reactant chamber 35 in the case of the anode, and with the ambient environment in the case of the cathode, and catalytic layers 27.2 which comprise a mixture of platinum black and polytetrafluoroethylene particles and 25.2 which comprise a mixture of platinum black and polytetrafluoroethylene particles. The catalyst layers are in contact with the electrolyte of the cell. The platinum is present in a loading of preferably 5–50 mg/cm$^2$, more preferably 5–30 mg/cm$^2$. The ratio of platinum to PTFE is preferably 10 to 3 on a weight basis. Reference electrode 29 is a porous, platinum catalyzed PTFE diffusion electrode which is approximately 7 mils thick. A fixed potential of 0.15 volts with respect to a reversible hydrogen electrode in the same electrolyte is maintained on the anode by means of the reference electrode through the potentiostat 24. The anode, cathode and reference electrode of the cell are connected through the electrical circuit, shown in FIG. 3. The electrochemical cell of the sensor 21 is connected to the circuitry so that the polarity of the working electrode (anode) to the counter electrode (cathode) is positive.

The circuitry whereby the maintenance of a fixed relative potential between the working electrode and reference electrode is shown in FIG. 3. FIG. 3 depicts a potentiostat circuit which is generally arranged in accordance with conventional principles within the knowledge of those skilled in the art and which enables the maintenance of the fixed relative potential between the working electrode and the reference electrode without development of current flow therebetween. The circuit also operates to enable appropriate current flow in the external circuit between the working electrode and the counter electrode when the gas to be detected is reacted within the electrochemical cell.

In FIG. 3, the electrochemical cell 21 is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92 and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected thereacross. The reference electrode 74 is connected to the operational amplifier 80 through a lead 102 and as the relative potential between the reference electrode 74 and the anode 70 develops a tendency to vary from the fixed level established by adjustment of the rheostat 92, the amplifier 80 operates through a negative feedback to maintain constant the relative potential between the anode 70 and the reference electrode 74. The factor creating the tendency to alter the anode-reference electrode fixed relative potential is developed as a result of reaction at the anode 70 of the impurity to be detected, i.e., oxidation of CO contained within the gas sample flowing across the face of the anode 70 as indicated by the arrow 104. The output current of the operational amplifier 80 will pass through the resistor 98 and will be a result of and related to the level of oxidation occurring at the anode 70. Therefore, the reading taken at the voltmeter 100 will be representative of the oxidation reaction occurring at the anode 70 and the quantity of material oxidized. The voltmeter 100 may be readily calibrated in the known manner to provide determination of the quantity of CO occurring in the air sample taken, and if the conditions in the anode chamber are in accordance with the teachings previously set forth, appropriate readings may be generated pursuant to the principle of operation provided.

An example of a preferred reactor is shown in FIG. 4. FIG. 4 depicts a portable microreactor 17 which is comprised of a Vycor tube 17' having an inlet 19 and an outlet 20. The tube 17' is surrounded by three separate insulation layers 50, 52 and 54. The first layer 50 is approximately 0.7 cm thick of high temperature moldable ceramic insulation (WRP-X Felt) which upon hardening rigidly holds both a heater wire 55 preferably of nichrome and a thermocouple wire 57, preferably of chromelconstantan thermocouple 57. The thermocouple wire 57 is connected to a temperature control and indicator 59 which can be of the conventional type. The second layer 52 is approximately 1.27 cm thick high temperature insulation such as a high temperature quilted blanket type insulation of minimum thermal conductivity (e.g., High Temp. MIN-K, Johns Manville Co.). The third layer 54 is approximately 1.27 cm thick low temperature insulation (e.g. MIN-K, Johns Manville Co.). The overall length of the reactor is about 26 cm while the length of the insulation layers 52 and 54 is about 15.2 cm. The heating wire 55 is connected via mechanical electrical junction 61 and 63, respectively, to a power source 65 such as regulated A.C. line voltage or by a battery pack consisting of eight size "D" nickel/cadmium cells. In the A.C. operating mold, the battery pack is continuously charged. The operating life between battery recharge (i.e., time of portable operation) depends upon the specific reactor temperature. However, even at 800° C the reactor is capable of continuous portable operation for 2-3 hours. The temperature control circuit (not shown) is designed to interface with and operate directly from the chromel-constantan thermocouple sensor housed in the reactor insulation 57. Simultaneous to providing the temperature control, the output of the thermocouple is preferably amplified and displayed on a 0-1 V panel meter (not shown).

In operation the detection device of the present invention functions as follows. An atmospheric gas sample containing hydrogen and carbon monoxide is introduced by the action of pump 15 at a metered rate into sealed sensor 21, passing in route thereto through filter 16, reactor 17 and connector 18. In CO sensor 21, the gas sample passes over the anode therein setting off electrooxidation of the CO impurity contained therein. This electrochemical reaction produces a current in the external circuit cell thereby enabling detection and measurement of the CO impurity as by the use of a voltmeter. In general the gas samples analyzed by the above procedure will ordinarily contain up to 3.5% hydrogen and up to 1000 ppm carbon monoxide.

The following examples are included to illustrate the importance of the temperature and non-catalytic reaction conditions in the oxidation step of the invention from the standpoint of selectively oxidizing hydrogen in the presence of carbon monoxide.

EXAMPLE 1

Palladium supported on silica gel containing 0.01 weight percent palladium was prepared by stirring silica gel in an aqueous solution of $PdCl_2.2H_2O$ in triply distilled water, subsequently evaporating the slurry to dryness, and then reducing at 578 K for 8 hours in a stream of pure hydrogen. The catalyst thus prepared was placed within the Vycor tube 17' of the microreactor 17 and catalytic reactions were studied therein. The amount of catalyst in the reactor was 25 mg for all runs.

The reactor was located in a flow system equipped with a dilution manifold to produce gas mixtures of CO (100 ppm), $H_2$ (1.3%), with the balance air. The gas mixtures were produced by mixing the constituents from a continuous stream in a glass bottle, and a sampling stream was drawn from this bottle at a constant flow rate through the reactor tube.

Septum sealed syringe sampling ports were placed before and after the reactor and in the sample bottle so that samples could be obtained of each gas mixture for analysis. Hydrogen, oxygen and carbon monoxide were analyzed by gas chromatography using a 5 A molecular sieve column for separation, UHP $N_2$ carrier gas, and a thermal conductivity detector for $H_2$ and $O_2$ analysis and an electrochemical detector for CO analysis.

In each experiment the flow rate of the gas mixture and temperature of the catalyst (contact time) were maintained constant and the gas compositions at all these sampling locations were monitored to ensure that gas mixtures were not varying and that steady-state was obtained in the reactor. The flow rate was 200 cc/minute at the selected catalyst temperatures. The results of the runs are shown in FIG. 5.

EXAMPLE 2

The procedure of Example 1 was followed but in the absence of catalyst. The results of the experimental runs are summarized in the graph of FIG. 6.

Figure 5:
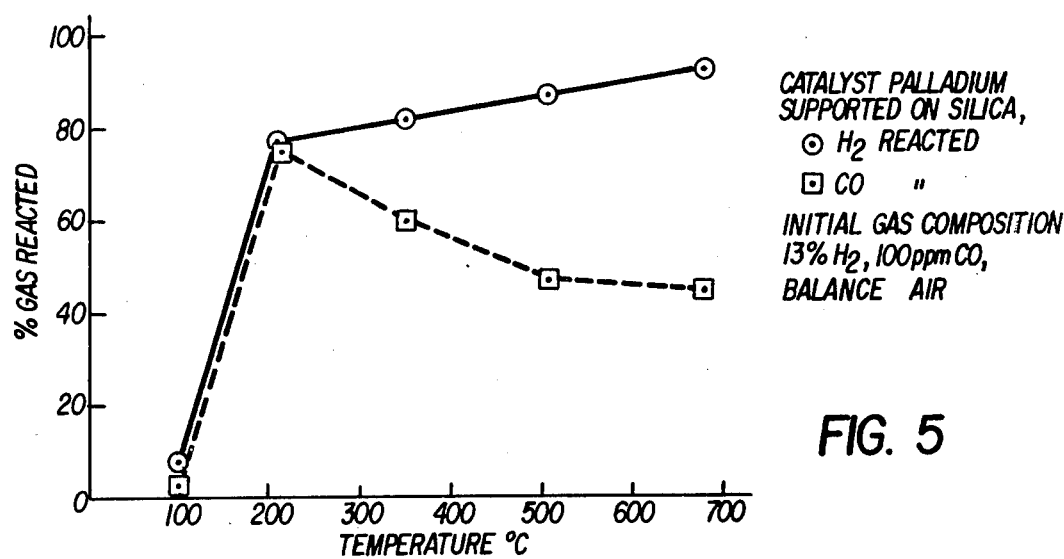
FIG. 5 is a graph showing the results of the oxidation of a hydrogen-carbon monoxide mixture in the presence of catalyst.
Figure 6:
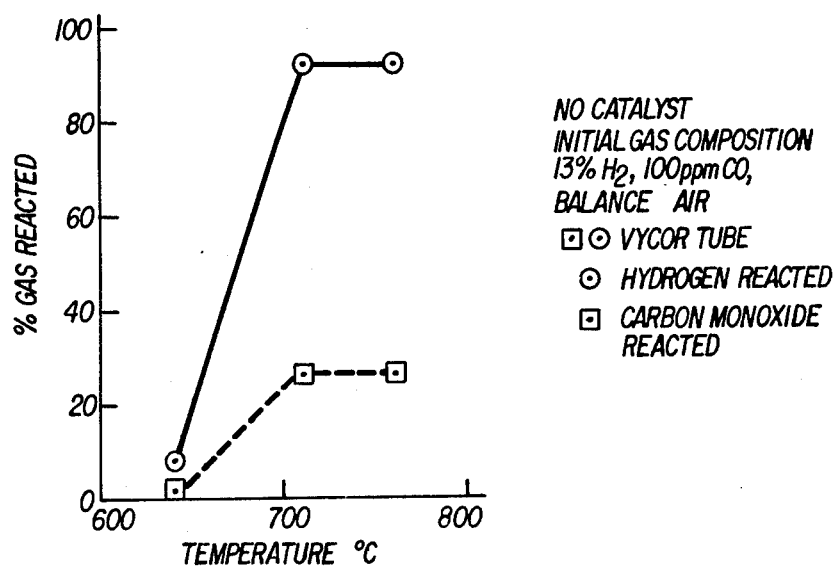
FIG. 6 is a graph showing the selective oxidation process of the present invention carried out in the absence of catalyst.

Comparing FIGS. 5 and 6, it can be seen from FIG. 5 that the presence of an oxidizing catalyst even at elevated temperatures is unable to provide an efficient selective oxidation of hydrogen in the presence of CO. For instance, at 675° C, as much as 45% of the CO is oxidized along with 92% of the hydrogen. In contrast, as shown in FIG. 6 carrying out the oxidation step in accordance with the present invention, that is, temperatures in excess of 700° and in a non-catalytic reaction zone, permits a significantly better separation of hydrogen from the carbon monoxide. For instance, at temperatures of 715° C, only 28% of the carbon monoxide is oxidized and 95% of the hydrogen. This difference in the oxidation of the respective constituents permits accurate measurements to be made by the CO sensor.

It is claimed:

1. A method for the detection of carbon monoxide in the presence of interfering concentrations of hydrogen which comprises heating a gas sample containing said carbon monoxide and hydrogen in an oxidizing atmosphere at a temperature of at least 700° C in a non-catalytic reaction zone to selectively oxidize the hydrogen to water, and passing the gaseous reaction product from the selective oxidation to an electrochemical carbon monoxide detection instrument.

2. The method of claim 1 wherein the gaseous reaction product from the selective oxidation is passed to the anode of an electrochemical cell comprising an anode, a reference electrode, a cathode, and an aqueous electrolyte in contact with said anode, cathode and reference electrode, said anode having catalyst bonded to a hydrophobic material to provide a diffusion electrode, said electrode is maintained at a fixed potential from about 0.7 to 1.5 volts with respect to the reversible hydrogen couple in the electrolyte of said cell, and the current flowing between said anode and cathode of said cell is measured to quantitatively determine the amount of carbon monoxide in said gaseous sample.

3. The method of claim 1 wherein the reaction temperature in said non-catalytic reaction zone is about 700° to 850° C.

4. An apparatus for detecting carbon monoxide in gas samples containing interfering concentrations of hydrogen in admixture with said carbon monoxide which comprises a reactor comprising a non-catalytic reaction zone, inlet and outlet means to and from said reaction zone, means for heating said reaction zone to a temperature in excess of about 700° C in combination with an electrochemical carbon monoxide detection instrument, communication means between said detection instrument and the outlet of said reaction zone, means for drawing said gas sample through said reaction zone and into said detection instrument at a controlled flow rate and read out means for reading the quantity of carbon monoxide detected.

5. The apparatus of claim 4 wherein the electrochemical instrument comprises a three-electrode chemical system having an electrochemical cell comprising an anode, a cathode, a reference electrode at which substantially no current flows and an aqueous electrolyte in contact with said anode, cathode and reference electrode, means for exposing said anode to said gas, means for maintaining said anode at a fixed potential relative to the reference electrode from about 0.7 to 1.5 volts with respect to the reversible hydrogen couple in the electrolyte in said cell.

6. The apparatus of claim 5 wherein the hydrophobic material of the anode is a hydrophobic fluorocarbon.

7. The apparatus of claim 6 wherein the hydrophobic fluorocarbon is polytetrafluoroethylene.

8. The apparatus of claim 7 wherein the means for heating said reaction zone includes a temperature control and indicator.

9. The apparatus of claim 4 wherein the reaction zone is of a chemically-resistant and heat-resistant glass material.

* * * * *